(12) United States Patent
Ladika et al.

(10) Patent No.: US 9,592,294 B2
(45) Date of Patent: Mar. 14, 2017

(54) POLYALKOXYLATED ALCOHOLS AS EXCIPIENTS FOR PHARMACEUTICAL COMPOSITIONS

(71) Applicant: Dow Global Technologies LLC, Midland, MI (US)

(72) Inventors: Mladen Ladika, Midland, MI (US); Jin Zhao, Midland, MI (US); Michael L. Tulchinsky, Midland, MI (US); Thomas H. Kalantar, Midland, MI (US); J. Keith Harris, Midland, MI (US)

(73) Assignee: Dow Global Technologies LLC

( * ) Notice: Subject to any disclaimer, the term of this patent is extended or adjusted under 35 U.S.C. 154(b) by 0 days.

(21) Appl. No.: 14/649,721

(22) PCT Filed: Jan. 13, 2014

(86) PCT No.: PCT/US2014/011284
§ 371 (c)(1),
(2) Date: Jun. 4, 2015

(87) PCT Pub. No.: WO2014/149160
PCT Pub. Date: Sep. 25, 2014

(65) Prior Publication Data
US 2015/0374823 A1  Dec. 31, 2015

Related U.S. Application Data

(60) Provisional application No. 61/803,478, filed on Mar. 20, 2013.

(51) Int. Cl.
| | | |
|---|---|---|
| A61K 47/10 | (2006.01) | |
| A61K 31/095 | (2006.01) | |
| A61K 31/10 | (2006.01) | |
| A61K 9/48 | (2006.01) | |
| A61K 31/192 | (2006.01) | |
| A61K 31/58 | (2006.01) | |
| C08G 65/20 | (2006.01) | |
| A61K 31/343 | (2006.01) | |
| C08L 71/02 | (2006.01) | |

(52) U.S. Cl.
CPC ............ A61K 47/10 (2013.01); A61K 9/4866 (2013.01); A61K 31/095 (2013.01); A61K 31/10 (2013.01); A61K 31/192 (2013.01); A61K 31/343 (2013.01); A61K 31/58 (2013.01); C08G 65/20 (2013.01); C08L 71/02 (2013.01)

(58) Field of Classification Search
CPC .... A61K 31/045; A61K 31/095; A61K 47/10; A61K 31/10
See application file for complete search history.

(56) References Cited

U.S. PATENT DOCUMENTS

| | | |
|---|---|---|
| 6,147,131 A | 11/2000 | Mork et al. |
| 6,660,743 B1 | 12/2003 | Cances et al. |
| 2002/0076426 A1 | 6/2002 | Zirnstein et al. |
| 2005/0181967 A1 | 8/2005 | Ruland et al. |
| 2009/0011024 A1 | 1/2009 | Babcock et al. |
| 2011/0281810 A1 | 11/2011 | Petersen et al. |

FOREIGN PATENT DOCUMENTS

| | | |
|---|---|---|
| EP | 1178044 A1 | 2/2002 |
| JP | 2006188619 | 7/2006 |
| WO | 0076482 A1 | 12/2000 |
| WO | 2010122313 A1 | 10/2010 |

OTHER PUBLICATIONS

Pressly et al. J. Polym. Sci. A. Polym. Chem., 2011, vol. 49, No. 3, pp. 814-819.*
Cole, et al., Challenges and opportunities in the encapsulation of liquid and semi-solid formulations into capsules for oral administration, Advanced Drug Delivery Reviews, vol. 60, 2008, pp. 747-756.
Schamp, et al., Development of an in vitro/in vivo correlation for lipid formulations of EMD 50733, a poorly soluble, lipophilic drug substance, European Journal of Pharmaceutics and Biopharmaceutics, vol. 62, 2006, pp. 227-234.

(Continued)

Primary Examiner — Samira Jean-Louis

(57) ABSTRACT

The present invention relates to the use of polyalkoxylated alcohols of the formula R—O-(AO)—H, wherein R is a substituted or unsubstituted alkyl, alkenyl, alkynyl, aryl, aralkyl or heterocyclic group having 7 to 25 carbon atoms, (AO) is a polyoxyalkylene moiety of the composition (BO)m(EO)n(DO)r with random or blockwise arrangement of the constituting oxyalkylene units, wherein m, n and r represent the average number of oxybutylene (BO) units, oxyethylene (EO) units and oxyalkylene units derived from at least one epoxide selected from styrene oxide and alkylene oxides having from 5 to 10 carbon atoms (DO) per molecule of the polyalkoxylated alcohol, respectively, m being a number greater than or equal to 1, n being a number greater than or equal to 1 and r being a number in the range from 0 to 50 under the proviso that (m+n+r) is less than or equal to 200 and the ratio n/(m+r) is in the range of 1 to 20, as excipients in pharmaceutical compositions. Said polyalkoxylated alcohols enable very effective solubilization of poorly soluble active pharmaceutical ingredients in aqueous media. Solid or semi-solid pharmaceutical compositions comprising one or more such polyalkoxylated alcohol combined with at least one active pharmaceutical ingredient are further long term stable under typical storage conditions and can be readily provided in various dosage forms such as tablets and filled capsules.

13 Claims, 1 Drawing Sheet

(56) References Cited

OTHER PUBLICATIONS

Nielsen, et al., Bioavailability of probucol from lipid and surfactant based formulations in minipgs: Influence of droplet size and dietary state, European Journal of Pharmaceutics and Biopharmaceutics, vol. 69, 2008, pp. 553-562.

Zhou, et al., Solubilisation of drugs in worm-like micelles of block copolymers of ethylene oxide and 1,2-butylene oxide in aqueous solution, International Journal of Pharmaceutics, vol. 354, 2008, pp. 82-87.

Ribeiro, et al., Solubilisation of griseofulvin in aqueous micellar solutions of diblock copolymers of ethylene oxide and 1,2-butylene oxide with lengthy B-blocks, International Journal of Pharmaceutics, vol. 369, 2009, pp. 196-198.

Johansson, et al., Surfactants based on fatty acids and other natural hydrophobes, Current Opinion in Colloid & Interface Science, vol. 6, 2001, pp. 178-188.

Elsabahy, et al., Solubilization of Docetaxel in Poly(ethylene oxide)-block-poly(butylene/styrene oxide) Micelles, Biomacromolecules, vol. 8, 2007, pp. 2250-2257.

\* cited by examiner

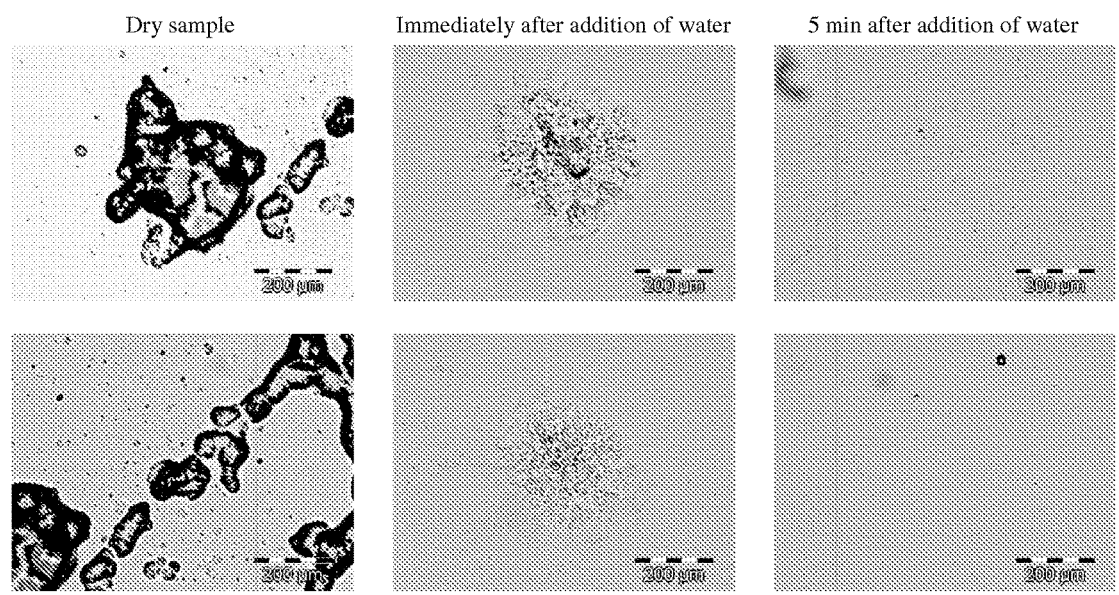

POLYALKOXYLATED ALCOHOLS AS EXCIPIENTS FOR PHARMACEUTICAL COMPOSITIONS

FIELD

The present invention relates to the use of certain polyalkoxylated alcohols as excipients to solubilize poorly soluble active pharmaceutical ingredients in aqueous media in order to enhance their bioavailability. Pharmaceutical compositions comprising such excipient and at least one active pharmaceutical ingredient, as well as various dosage forms comprising said pharmaceutical composition, are also within the scope of the invention.

INTRODUCTION

The majority of novel active pharmaceutical ingredients (APIs) suffers from poor aqueous solubility and concomitantly low bioavailability and efficacy, which frequently prevents their commercialization. New formulation strategies are thus required and have been developed aiming to overcome this problem. Herein, the API is typically combined with an excipient to enhance its solubility in aqueous medium. The excipient usually includes a surface-active substance comprising hydrophilic and lipophilic moieties, i.e. having an amphiphilic structure, which forms aggregates such as micelles in an aqueous environment above a critical micelle concentration. Lipophilic APIs can thus be solubilized by incorporation into the lipophilic interior of such aggregates. A broad variety of different substances have been investigated as excipients, e.g. oils, lipids, glycerides, fatty acids, fatty alcohols and derivatives such as polyalkoxylated derivatives of any of these, polymers such as polyethylene glycols, polypropylene glycols, polyethylene glycol methyl ethers, polyvinyl alcohols and polyoxyalkylene block copolymers, fatty acid esters of polyoxyethylene sorbitan, sodium lauryl sulphate, polyoxyethylene castor oil derivatives, vitamin E and derivatives thereof, hypromellose acetate succinate and mixtures thereof to name just a few (cf. for instance excipients mentioned in Handbook of Pharmaceutical Excipients, third Edition, edited by A. H. Kibbe, American Pharmaceutical Association and Pharmaceutical Press (2000); WO 00/76482 and Tables 3-5 in E. T. Cole et al., Advanced Drug Delivery Reviews 60 (2008), 747-756). However, most of the excipients known from the prior art yield only modest to moderate enhancements of the aqueous solubility of APIs. Consequently there remains a need for alternative physiologically compatible excipients that enable a more efficient solubilisation of APIs.

Substances of particular interest for use as more efficient excipients are polyalkoxylated alcohols since their structure determining the physicochemical interaction with water on the one hand and compounds to be solubilised on the other hand may be adjusted in a versatile manner by variation of the precursor alcohol and the type(s) of constituting oxyalkylene units, their relative amounts and arrangement. Higher alcohols alkoxylated with ethylene oxide, propylene oxide, butylene oxide or higher alkylene oxides and mixtures thereof are well-known non-ionic surfactants and emulsifiers. However, only a limited number of such compounds, mainly ethoxylated and/or propoxylated monoalcohols, have been suggested for use as solubilizers in pharmaceutical compositions so far.

For example, US 2002/0076426 A1 suggests the use of $C_{10}$ terpene alcohol ethoxylates comprising 3 to 10 moles of EO units to solubilize sparingly water-soluble or sparingly water-dispersible compounds in cosmetic or pharmaceutical preparations or in concentrates for food preparations. The terpene alcohol ethoxylates are reported to have an above-average solubilizing capability for sparingly water-soluble or -dispersible compounds if used in amounts of 3 to 90 wt. % based on the total weight of the preparation, and are physiologically compatible and chemically stable. However, in fact only a modest increase in the saturation drug concentration could be achieved in a phosphate buffer pH 7.0 by addition of the terpene alcohol ethoxylates in an amount of 20 wt. % based on the total weight of the solution compared to the phosphate buffer alone. Thus, for example the saturation drug concentration was increased by a factor of up to about 14 for the solubilization of sulfathiazole.

US 2011/0281810 A1 proposes the use of $C_{6-30}$ monoalcohols alkoxylated with ethylene oxide, propylene oxide, butylene oxide or mixtures thereof, characterized by comprising at least one oxypropylene unit, as solubilizers for poorly water-soluble drugs in pharmaceutical compositions. Different polyoxypropylene ethers and polyoxypropylene-polyoxyethylene ethers of fatty alcohols commercially available under the trademark Eumulgin were tested as solubilizers for diazepam, erythromycin, itraconazole, estradiol and several cinnamate derivatives as model substances of lipophilic APIs. It is demonstrated that the oxypropylene-containing polyethers according to the teaching of US 2011/0281810 A1 are better solubilizers than prior art ethoxylated monoalcohols containing no oxypropylene unit. However, the achieved maximum increase of aqueous solubility by a factor of about 170 as obtained for diazepam with Eumulgin HPS is still only moderate. Moreover, Eumulgin RO 35 PH, an ethoxylated castor oil, ranged consistently among the most efficient solubilizers for all investigated lipophilic model substances with the exception of estradiol and mostly showed more efficient solubilisation than the oxypropylene-containing polyether alcohols according to the teaching of US 2011/0281810 A1.

Furthermore, EP 1 178 044 A1 describes polyalkoxylated tocopherol derivates obtainable by stepwise base-catalyzed alkoxylation of vitamin E or its derivatives with ethylene oxide and at least one epoxide selected from propylene oxide and butylene oxide as potent emulsifiers for the use in pharmaceutical and cosmetic formulations. However, vitamin E and its derivatives represent rather expensive starting compounds and in some applications physiological effects imparted by the tocopheryl moiety may not be desired.

In view of the foregoing, the present invention thus aims to provide alternative compounds for the use as excipients in pharmaceutical formulations, which enable a more efficient solubilisation of APIs in aqueous media than conventional excipients known from the prior art, are physiologically compatible, provide long-term stable API/excipient formulations and can be prepared cost-efficiently from readily available resources. It is a further objective of the present invention to provide the corresponding API/excipient formulations in dosage forms with high patients' acceptance.

SUMMARY

In a first aspect, the present invention thus relates to a solid or semi-solid pharmaceutical composition comprising
a) at least one active pharmaceutical ingredient (API), and
b) at least one polyalkoxylated alcohol of the formula

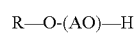

wherein R is a substituted or unsubstituted alkyl, alkenyl, alkynyl, aryl, aralkyl or heterocyclic group having 7 to 25 carbon atoms, (AO) is a polyoxyalkylene moiety of the composition $(BO)_m(EO)_n(DO)_r$ with random or blockwise arrangement of the constituting oxyalkylene units, wherein m, n and r represent the average number of oxybutylene (BO) units, oxyethylene (EO) units and oxyalkylene units derived from at least one epoxide selected from styrene oxide and alkylene oxides having from 5 to 10 carbon atoms (DO) per molecule of the polyalkoxylated alcohol, respectively, m being a number greater than or equal to 1, n being a number greater than or equal to 1 and r being a number in the range from 0 to 50 under the proviso that (m+n+r) is less than or equal to 200 and the ratio n/(m+r) is in the range of 1 to 20.

In another aspect, the present invention is directed towards the use of the polyalkoxylated alcohol as defined in the context of the pharmaceutical composition according to the present invention to increase the solubility and/or the dissolution rate of an active pharmaceutical ingredient in an aqueous medium and/or to increase the bioavailability of an active pharmaceutical ingredient.

In another aspect, the present invention is directed towards a method of increasing the solubility and/or the dissolution rate of an active pharmaceutical ingredient in an aqueous medium and/or of increasing the bioavailability of an active pharmaceutical ingredient which comprises the step of blending the active pharmaceutical ingredient with a polyalkoxylated alcohol as defined herein.

Furthermore the present invention is related to a solid or semi-solid dosage form comprising a pharmaceutical composition according to the invention.

The present invention is based on the surprising finding that polyalkoxylated alcohols as set forth above as component b) of the inventive composition may dramatically enhance the solubility and/or dissolution rate of APIs, especially those with a low intrinsic aqueous solubility, in aqueous media, e.g. increasing the aqueous solubility of several lipophilic model drugs by a factor on the order of 3 to 4 orders of magnitude. Accordingly the polyalkoxylated alcohols according to the invention enable a significantly more efficient solubilisation of APIs than conventional prior art excipients and provide concomitantly better API bioavailability. The advantageous dissolution characteristics are retained upon storage for several months even under accelerated ageing conditions evidencing physical and chemical stability of the inventive pharmaceutical compositions. Without being bound to any particular theory, the inventors are of the opinion that the specific composition of the polyalkoxylated alcohols with a combination of an essentially nonpolar group R of considerable length having 7 to 25 carbon atoms at one end and bound thereto a polyoxyalkylene moiety with an average degree of alkoxylation of maximum 200 that contains EO units in a specific ratio (at least equimolar amount up to a 20-fold molar excess) to BO units and optionally additionally present higher oxyalkylene units provides an amphiphilic structure with a well balanced ratio of constituting hydrophilic versus lipophilic moieties to enable a very efficient solubilisation of various APIs. The polyalkoxylated alcohols according to the invention represent further non-toxic, physiologically compatible substances and can be prepared in a cost-efficient manner from readily available resources using established techniques and equipment conventionally employed for the alkoxylation of alcohols. The inventive polyalkoxylated alcohols typically yield solid or semi-solid formulations when combined with one or more API and can be provided in dosage forms of high patients' acceptance such as tablets or filled capsules using processing techniques and equipment being well established in the pharmaceutical industry. Due to the efficient API solubilisation, an effective dose as required for most medical treatments in-vivo may usually be provided by a single unit of a tablet or filled capsule of conventional size and within a short time from administration.

BRIEF DESCRIPTION OF DRAWINGS

FIG. 1 illustrates the dissolution of a freeze-dried pharmaceutical composition according to the invention (Example T-7 of Table 4) comprising Probucol as a lipophilic drug and a polyalkoxylated alcohol according to the present invention obtained by alkoxylation of 2-ethyl-hexanol first with 4 equivalents of 1,2-butylene oxide and subsequently with 24 equivalents of ethylene oxide (excipient of Example C-2) in water by showing two series of microscopic images each taken at 10× magnification in the dry state, immediately after and 300 s after the addition of water.

DESCRIPTION OF EMBODIMENTS

Further features and advantages of the invention will be explained in detail below.

As pointed out above, the composition of the polyalkoxylated alcohol is a key aspect of the present invention. The polyalkoxylated alcohol is generally of the formula R—O—(AO)—H. The group R can be a substituted or unsubstituted alkyl, alkenyl, alkynyl, aryl, aralkyl or heterocyclic group having 7 to 25 carbon atoms, preferably 8 to 20 carbon atoms, more preferably 9 to 18 carbon atoms or most preferably 10 to 18 carbon atoms. As far as these groups contain non-cyclic moieties these can be linear or branched. If substituted, the alkyl, alkenyl, alkynyl, aryl, aralkyl or heterocyclic group may contain one or more functional groups. The one or more functional groups can each individually e.g. be selected from a hydroxyl, ether, thiol, thioether, carboxyl, amine, ester, amide, cyano, isocyanate, thioisocyanate, carbamate, epoxy or halogen group. Preferably the group R is unsubstituted. In a particularly preferred embodiment of the present invention the group R is a hydrocarbyl group, preferably an ethylenically saturated or internally unsaturated hydrocarbyl group. Herein, internally unsaturated means the presence of at least one bond selected from $R^1R^2C = CR^3R^4$ and $R^5C \equiv CR^6$ in the molecule, wherein $R^1$, $R^2$, $R^3$ and $R^4$ are each individually selected from a hydrocarbyl and a hydrogen radical under the proviso that neither $R^1$ and $R^2$ nor $R^3$ and $R^4$ are at the same time hydrogen, and $R^5$ and $R^6$ each represent a hydrocarbyl radical, meaning in other words that R comprises no terminal unsaturated group. Suitable non-limiting examples of the group R are for instance heptyl, capryl, 2-ethyl-hexyl, nonyl, decyl, undecyl, lauryl, myristyl, cetyl, palmitoleyl, stearyl, isostearyl, oleyl, linoleyl, ricinoleyl, arachidyl, behenyl, lignoceryl, benzyl, xylyl, ethylbenzyl, cinnamyl, butylphenyl, amylphenyl, heptylphenyl, octylphenyl, nonylphenyl, dodecylphenyl, naphthyl, indolyl, menthyl, geranyl, neryl, linaloyl, terpenyl, citronellyl, thymyl, bornyl, farnesyl, geranyl or myrtenyl including all possible isomeric and enantiomeric forms of these compounds.

The group R is bound by an ether bond to a polyoxyalkylene moiety (AO). The polyoxyalkylene moiety (AO) is a polyether chain that constitutes of oxyethylene (EO), oxybutylene (BO) and, optionally, oxyalkylene units derived from at least one epoxide selected from styrene oxide and alkylene oxides having from 5 to 10 carbon atoms (DO) generally having a composition of $(BO)_m(EO)_n(DO)_r$. Herein, m, n and r denote the average number of BO, EO and DO units per molecule of the polyalkoxylated alcohol, respectively, and are generally floating point numbers. The length of the formed polyether chains in the polyalkoxylated polyalcohol in terms of the number of constituting oxyalkylene units varies typically statistically about an average value, which theoretically corresponds to the sum of the equivalents of alkylene oxides used for alkoxylation of the alcohol. The molecular structure and chemical composition of polyalkoxylene moieties can be determined by methods well-known in the art as for example reviewed in "Nonionic Surfactants-Polyoxyalkylene Block Copolymers", edited by V. M. Nace, Surfactant Science Series, vol. 60 (1996). The molecular weight distribution of the polyalkoxylated alcohols as well as of intermediates occurring in the preparation thereof may in particular be determined e.g. by size exclusion chromatography (SEC) or by liquid chromatography/electrospray ionization-mass spectrometry (LC/ESI-MS) as explained in detail in the Examples. As set forth in the Examples, the average total degree of alkoxylation and the average number of oxyalkylene units of a certain type per molecule of the polyalkoxylated alcohol may be deduced from such molecular weight data.

The polyoxyalkylene moiety (AO) of the polyoxyalkylated alcohols according to the present invention is characterized by m being a number greater than or equal to 1, preferably being at least 2, more preferably being at least 4, n being a number greater than or equal to 1, preferably being at least 8, more preferably being at least 12, even more preferably being more than 20 such as greater than or equal to 21, and r being a number in the range from 0 to 50, preferably in the range from 0 to 5, more preferably being 0, under the proviso that the total degree of alkoxylation (m+n+r) is less than or equal to 200, preferably less than or equal to 100, more preferably less than 50, and that the ratio n/(m+r) is in the range from 1, preferably from 1.5, more preferably from 1.8, to 20, preferably to 10, more preferably to 7. In a particularly preferred embodiment of the present invention the polyoxylkylene moiety of the polyalkoxylated alcohol comprises only EO and BO units, i.e. the parameter r is 0.

The constituting oxyalkylene units can be arranged randomly or blockwise in the polyoxyalkylene moiety (AO). Random arrangement includes polyether structures wherein the distinct types of constituting oxyalkylene units are distributed statistically homogeneously over the polyether chains as well as polyether structures wherein at least one type of oxyalkylene units is preferentially bound to units of either the same type or a distinct type of oxyalkylene units. In a specific embodiment of the present invention the polyoxyalkylene moiety (AO) of the polyalkoxylated alcohol contains a hydrophobic block that comprises predominantly oxybutylene units and is bound to the RO-terminated end, and a hydrophilic block comprising predominantly of oxyethylene units further to the hydroxyl-terminated end. The term predominantly may mean herein that on average at least 60 mol % or preferably at least 80 mol % of the oxyalkylene units constituting the respective block are of the designated type. In a preferred embodiment of the present invention the polyalkoxylated alcohol has a diblock structure according to the formula R—O—(BO)$_m$-(EO)$_n$—H, wherein R, BO, EO, m and n are as defined above. In a particularly preferred embodiment of the present invention such diblock polyalkoxylated alcohol is employed, wherein m is at least 4, n is at least 12, preferably more than 20, and (m+n) is less than or equal to 100, preferably less than or equal to 50, under the proviso that the ratio n/m is in the range of 1.5 to 10, preferably 1.8 to 7.

The afore-mentioned polyalkoxylated alcohols according to the present invention can be obtained by alkoxylation of an alcohol with ethylene oxide and butylene oxide and, optionally, one or more epoxides selected from styrene oxide and alkylene oxides having from 5 to 10 carbon atoms in a manner known per se from the prior art (see e.g. Nikolaus Schönfeldt, Grenzflächenaktive Äthylenoxid-Addukte, Wissenschaftliche Verlagsgesellschaft mbH Stuttgart, 1984 and I. Johansson, M. Svensson, Current Opinion in Colloid & Interface Science 6 (2001) 178-188 for common non-limiting alkyoxylation conditions). The addition reaction is typically carried out in a closed reactor such as an autoclave with stirring means at a temperature in the range from 90 to 200° C., preferably from 120 to 180° C., at a pressure of up to about 10 bar. Usually strong bases such as alkali metal hydroxides or alkali metal alkoxides are employed to catalyze the alkoxylation reaction. Alkali metal alkoxide catalyst may favorably also be formed in-situ by adding alkali metal to the precursor alcohol being provided in the reactor either as neat substance or as a solution in an inert solvent. Alternatively also Brönsted acids, Lewis acids such as $AlCl_3$, $BF_3$, $SbCl_5$ or $SnCl_4$, or double metal cyanide compounds such as those described in US 2005/0181967 may be used as catalysts. The catalyst is used in an amount generally in the range from 0.001 to 5 wt. %, mostly in a range from 0.1 to 2 wt. %, based on the total mass of the precursor alcohol and may be added as neat substance or dissolved in a solvent to the precursor alcohol provided in the reactor. Prior to the metered addition of the alkylene oxides the reaction mixture may be dewatered at a temperature in the range of 50 to 110° C. under reduced pressure, if required. The ethylene oxide, butylene oxide and the other optional epoxides, if used, can be metered into the reaction mixture simultaneously or sequentially. They may be diluted with an inert gas. Introducing two or more alkylene oxides simultaneously leads to a random arrangement of the corresponding oxyalkylene units in the polyether chain. Sequential addition of the alkylene oxides with sufficient time in between the distinct addition steps to allow for a substantially complete reaction before adding the next alkylene oxide results on the contrary in a blockwise distribution of the oxyalkylene units in the polyether chain. For instance the precursor alcohol would be reacted in a first stage with the complete amount of butylene oxide before introducing ethylene oxide in a second step in case of the preparation of a diblock polyalkoxylated alcohol of the formula R—O—(BO)$_m$-(EO)$_n$—H as set forth above. By controlling the relative amounts of the employed different alkylene oxides added to the reaction mixture over time, the composition of the polyether chain segments that form progressively during the preparation process may continuously be varied from homoblocks over segments with a graded distribution of more than one type of constituting oxyalkylene unit to segments with a constant random distribution of multiple types of constituting oxyalkylene units. For example an amphiphilic polyalkoxylated alcohol with a polyether chain having a hydrophobic segment bound to the RO-terminated end and a hydrophilic segment further to the other terminus could be obtained by metering in the beginning of the preparation process mainly or exclusively butylene oxide optionally plus styrene oxide and/or alkylene oxides having from 5 to 10 carbon atoms into the reaction mixture and reducing their amount relative to the metered amount of ethylene oxide gradually or stepwise within the course of the preparation process. In any case, ethylene oxide, butylene oxide and the optional additional epoxides, if present, are each typically used in a total amount that corresponds to the respective average stoichiometric value n, m or r in the targeted compound, calculated on the molar amount of the precursor alcohol in the starting reaction mixture assuming complete consumption of the added alkylene oxides in the alkoxylation of the alcohol component. After the reaction has been completed, the catalyst can be neutralized e.g. by the addition of an acid or a base and the reaction mixture be filtrated. The obtained product may then be used directly or after further purification by conventional means to remove unreacted starting compounds or byproducts, if any.

Ethylene oxide, butylene oxide and the further epoxides optionally used to prepare the polyalkoxylated alcohols according to the present invention such as styrene oxide represent basic commercially available chemicals that are obtainable by epoxidation of the corresponding olefins e.g. by the hydrochlorination route or by direct catalytic oxidation. The butylene oxide used in the alkoxylation reaction can be 1,2-butylene oxide, 2,3-butylene oxide or a mixture thereof. Preferably 1,2-butylene oxide is employed. As precursor alcohol any alcohol of the formula R—OH, wherein the group R has the same meaning as defined above, or a mixture of two or more of such alcohols can be used in the alkoxylation reaction. In a preferred embodiment of the present invention the polyalkoxylated alcohol is derived by alkoxylation of a precursor alcohol R—OH available from renewable natural resources. Suitable precursor alcohols available from renewable natural resources can for instance be fatty alcohols such as e.g. lauryl alcohol, cetyl alcohol, stearyl alcohol, cetostearyl alcohol, myristyl alcohol, oleyl alcohol and cocoyl alcohol and, particularly preferable, terpene alcohols such as e.g. geraniol, nerol, farnesol, linalool, menthol, terpineol, citronellol, borneol, myrtenol and dihydrocarveol, including all available isomeric and enantiomeric forms of these compounds. Fatty alcohols can be derived from vegetable feedstocks such as coconut oil, palm oil, jojoba oil or rapeseed by transesterification and subsequent hydrogenation and are additionally also produced on a petrochemical basis. Terpene alcohols are contained in the essential oils from many plants and can be extracted therefrom or be obtained by chemical derivatisation of suitable terpenoid precursors. The polyalkoxylated alcohols according to the present invention can thus be obtained from starting compounds that are readily commercially available and at least partly based on renewable natural resources, using established alkoxylation techniques in a cost-efficient and sustainable manner.

The polyalkoxylated alcohols of the above-described kind have been found to be very efficient in the solubilization of active pharmaceutical ingredients (APIs). Accordingly a polyalkoxylated alcohol according to the present invention or a mixture of two or more thereof can be used to increase the solubility and/or the dissolution rate of an active pharmaceutical ingredient in an aqueous medium. Herein, increase of solubility means that the amount of substance, which is dissolved and/or dispersed in the aqueous medium in a manner that the aqueous medium remains visually clear and transparent, is increased. The aqueous medium within the sense of the present invention can e.g. be water itself as well as any kind of physiologically relevant aqueous solution. Physiologically relevant aqueous solutions are natural aqueous body fluids of humans and animals, and artificially prepared aqueous solutions that mimic such body fluids or are representative of an aqueous medium in a certain physiological state, respectively. Examples of physiologically relevant aqueous solutions are for instance saliva, blood, gastric fluid, intestinal fluid, simulated gastric fluid, fasted state simulated intestinal fluid, fed state simulated intestinal fluid and other aqueous buffer and/or enzyme solutions simulating further physiological conditions.

The active pharmaceutical ingredient can generally be any substance for application in a therapeutic, diagnostic or prophylactic medical treatment of the human or animal body. The API may for instance be selected from the group of antihypertensives, anti-anxiety agents, anticlotting agents, anticonvulsants, blood glucose lowering agents, decongestants, antihistamines, antitussives, beta blockers, anti-inflammatories, antipsychotic agents, cognitive enhancers, cholesterol-reducing agents, antiobesity agents, autoimmune disorder agents, anti-impotence agents, antibacterial agents, antifungal agents, hypnotic agents, anti-Parkinsonism agents, anti-Alzheimer's disease agents, anti-depressants, antiviral agents, anti-atherosclerotic agents, glycogen phosphorylase inhibitors, hormones, vitamins, carotinoids, antiseptic agents, cytostatics, anesthetics, neuroleptics, antimycotics, spasmolytic agents, immunoglobines, sera, thyroid therapeutic agents, antihyperkinetic agents, ophthalmic agents, neuropathy agents, metabolic regulators, muscle relaxants, anti-lipemics, hepatic therapeutic agents, coronary agents, cardiacs, regulatory peptides and enzymes and their inhibitors, sedatives, gynecological agents, gout remedies, fibrinolytics, circulation-promoting agents, diuretics, diagnostic agents, corticoids, bile duct therapeutics, antiasthmatics, anti-epileptics, antidotes, antidiabetes agents, antiallergics, analgesics, analeptics, keratolytic agents, antipyretic agents and vasodilatory agents, without being limited thereto. The present invention is particularly useful when the API is poorly soluble in aqueous medium such as a class II drug according to the Biopharmaceutics Classification System (BCS) as these substances typically suffer from an insufficient bioavailability. Poorly soluble in aqueous medium means within this invention that the API alone has a solubility of 50 mg/L or less, preferably 10 mg/L or less, more preferably 1 mg/L or less, in aqueous medium, which is distilled water of pH 7.0 if not indicated otherwise, at a temperature of 22° C. and an atmospheric pressure of 1 atm. The solubility of the API in an aqueous medium can be determined quantitatively e.g. by high pressure liquid chromatography analysis as set forth in detail in the Examples. The polyalkoxylated alcohols according to the invention may increase the solubility of an API dramatically such as by 3 to 4 orders of magnitude, e.g. by a factor of more than 5,000 as demonstrated for the lipophilic model drug Probucol. The polyalkoxylated alcohols according to the present invention may concomitantly efficiently enhance the bioavailability of an API e.g. by forming molecular aggregates such as micelles as vehicles. Lipophilic APIs may effectively be dissolved in the interior of these vehicles. The vehicles are stable in the surrounding aqueous medium and allow transporting the API in amounts significantly higher than without use of the polyalkoxylated alcohol to sites in a human or animal body, where they exert their pharmacological effect. Moreover, the dissolution of an API in aqueous medium may be significantly accelerated when using additionally a polyalkoxylated alcohol according to the present invention as excipient, e.g. the dissolution process may be essentially accomplished within less than 300 s, in many cases in less than 30 s. Observation techniques such as optical microscopy or time-resolved turbidity measurements enable following the temporal progress of the dissolution process and provide at least a qualitative measure of the dissolution rate.

The afore-mentioned favorable dissolution characteristics of mixtures of at least one API with one or more polyalkoxylated alcohols according to the present invention are retained over considerable periods of time under typical storage conditions such as 4 months at ambient conditions (22° C. and 50% relative humidity (RH)) evidencing the physical and chemical stability of such API/excipient formulations. The inventive formulations may even be stable when exposed to accelerated ageing conditions such as storage at a temperature of 40° C. and 75% RH for 4 months.

Pharmaceutical compositions according to the present invention comprise at least one polyalkoxylated alcohol as defined above and at least one active pharmaceutical ingredient as set forth above. Typically these inventive pharmaceutical compositions are solid or semi-solid at ambient conditions (22° C., 1 atm). Solid means that the material retains its shape and volume when not confined. A solid material typically does not deform or flow when an external force is applied. Semi-solid means that the material deforms and/or flows slowly when an external force such as gravity is applied. A semi-solid material has a rigidity and viscosity that is lower than the rigidity and viscosity of a solid material but higher than the rigidity and viscosity of a liquid. The solid and semi-solid state thus differs from the liquid state in that the latter is characterized by the material being flowable even in the absence of any external force and unable to retain any shape when not confined. Of course it is readily understood by the skilled artisan that a mass of discrete solid particles, such as a powder or a granular material, is classified as a solid material although only the individual particles retain their shape and volume when not confined, but not the entire mass. Typically the semi-solid pharmaceutical compositions according to the present invention exhibit a viscosity as measured with a Brookfield viscosimeter such as a Brookfield RV DV-II+ Pro instrument at a temperature of 22° C. using a #5 spindle and a rotational speed of 3 rpm in the range of 5,000 mPa·s to 1,000,000 mPa·s.

Besides the at least one polyalkoxylated alcohol and the at least one active pharmaceutical ingredient the pharmaceutical composition according to the present invention may comprise further one or more physiologically compatible additives. Any conventional additives used in pharmaceutical compositions known from the prior art can be employed as long as they do not interfere with the action of the active pharmaceutical ingredient and do not adversely affect the above-described favorable effects imparted by the polyalkoxylated alcohol. If present in the inventive pharmaceutical composition, the at least one optional additive may for instance be selected from the group of fillers, pH regulators, solvents, surfactants, antioxidants, preservative agents, plasticizers, coloring agents, flavouring agents, mineral adjuvants, emollients, lubricants, perfumes and excipients other than the polyalkoxylated alcohols according to the present invention and mixtures of any of the foregoing. Suitable antioxidants can be exemplified by ascorbic acid, citric acid, vitamin E and derivatives of these compounds, as well as butylated hydroxyanisole. As plasticizer for instance mineral oils, petrolatum, lanolin, polyethylene glycol, polypropylene glycol, sorbitol, triethanol amine, benzyl benzoate, dibutyl sebacate, diethyl phthalate, glyceryl monostearate, triacetin and/or triethyl citrate could be used. Suitable solvents are e.g. water, alcohols such as ethanol, isopropyl alcohol, ethylene glycol, propylene glycol, polyethylene glycol, polypropylene glycol and glycerol. Eligible pH regulators can be all types of physiologically acceptable acids and/or bases. Suitable surfactants can be nonionic, cationic, anionic or of the betain type. For example fatty alcohol sulfates, fatty alcohol sulfonates, fatty alcohol ether sulfates, fatty alcohol ether sulfonates, fatty alcohol alkoxylates, fatty alcohol phosphates, fatty acid sulfonates, alkyl sulfonates, alkyl polyglycosides, sorbitan esters and alkoxylated derivatives thereof, sugar fatty acid esters, fatty acid polyglycerol esters, fatty acid partial glycerides, fatty acid carboxylates, fatty alcohol succinates, quarternary ammonium compounds, alkylphenol alkoxylates or mixtures thereof could be used, without being limited thereto. Fillers that may be incorporated in the pharmaceutical composition of the present invention e.g. to modify the consistency or appearance include, without being limited thereto, for instance pigments, titania, alumina, silica, zinc oxide, magnesium stearate, silicates, alumosilicates, clay, talc, waxes and polymers e.g. cellulose derivatives such as methyl cellulose, ethyl cellulose, hydroxyethyl cellulose or hydroxypropyl methylcellulose. Excipients other than the polyalkoxylated alcohols according to the present invention can be exemplified for instance by the substances mentioned as excipients in the Handbook of Pharmaceutical Excipients, Third Edition, Edited by A. H. Kibbe, American Pharmaceutical Association and Pharmaceutical Press (2000), WO 00/76482 and Tables 3-5 in E. T. Cole et al., Advanced Drug Delivery Reviews 60 (2008), 747-756.

The pharmaceutical composition according to the present invention may comprise the at least one active pharmaceutical ingredient and the at least one polyalkoxylated alcohol together in an amount corresponding to 1 to 100 wt. %, preferably at least 10 wt. %, more preferably at least 50 wt. % based on the total weight of the composition. The remainder of the pharmaceutical composition may then comprise physiologically compatible additives, if any. The additives may thus e.g. be comprised in a total amount corresponding to 0 to 99 wt. %, preferably 0 to 90 wt. % or 0 to 50 wt. % based on the total weight of the pharmaceutical composition. The at least one active pharmaceutical ingredient and the at least one polyalkoxylated alcohol are typically comprised in the pharmaceutical compositions according to the invention in a weight ratio in the range from 10:1 to 1:100, preferably from 5:1 to 1:10, more preferably in the range from 1:1 to 1:3. In one particular embodiment of the present invention the at least one polyalkoxylated alcohol is present in the pharmaceutical composition in an amount of more than 5 wt. %, preferably at least 10 wt. %, more preferably at least 25 wt. %, most preferably at least 50 wt. %, based on the total weight of the composition. The pharmaceutical composition according to the present invention can be substantially free of copper ions. Substantially free means that the designated chemical species, if present at all, are comprised in a concentration being so low that no measurable physiological effect results from this species. This is e.g. considered to be the case, if the concentration of copper ions is below 0.01 wt. % such as in a range from 0 to 0.005 wt. % based on the total weight of the pharmaceutical composition.

The pharmaceutical compositions according to the present invention can be prepared using conventional techniques and equipment. For instance formulations comprising at least one API combined with at least one polyalkoxylated alcohol of the present invention can be obtained by solution-based methods such as co-precipitation and spray drying. For spray drying a solution or dispersion comprising the at least one API and the at least one polyalkoxylated alcohol may be provided and sprayed into a heated gaseous drying medium to evaporate the solvent. Alternatively, also freeze-drying can be applied. Details of the spray drying process can e.g. be found in R. H. Perry, D. W. Green, J. O. Maloney eds., Perry's Chemical Engineers' Handbook, $6^{th}$ edition, McGraw-Hill Book Co. 1984, pages 20-57. Co-precipitation can be carried out for instance by dissolving the at least one API and the at least one polyalkoxylated alcohol in a mutual solvent and subsequent mixing with a non-solvent or again by removing the solvent through evaporation. Another possibility is to provide a first solution of the API component in a first solvent and a second solution of the polyalkoxylated alcohol component in a second solvent. The first solvent and the second solvent can be selected in such a manner that the solubility of both components is sufficiently low in the mixture of the first and the second solvent. Thus the at least one API and the at least one polyalkoxylated alcohol can be co-precipitated by mixing both solutions. In another possibility, the first solvent and the second solvent can be selected in such a manner that the solubility of both components is sufficiently high in the mixture of the first and the second solvent, and mixing of both solutions gives a clear solution of both components. Alternatively, the same solvent can be selected for dissolution of both components. Removal of the solvent(s) provides a solid or semi-solid mixture of the components. Furthermore the at least one API and the one or more polyalkoxylated alcohols may be combined into a formulation by a melt process. For instance the at least one API may be dissolved in the molten polyalkoxylated alcohol or a mixture of multiple polyalkoxylated alcohols using conventional melt extrusion techniques. The optional additives, if any, may be incorporated at any suitable stage of the preparation of the inventive pharmaceutical compositions such as by including them into the precursor solutions or dispersions or the feedstocks for melting, by adding them during the process used for combining the least one API and the one or more polyalkoxylated alcohols or by introducing them into the mixture obtained from this process. In the obtained product of the aforementioned preparation processes the API and polyalkoxylated alcohol components may be present as a solid dispersion or the API may be dissolved in the phase comprising the one or more polyalkoxylated alcohols or be dispersed therein, wherein the dispersed API phase preferably exhibits a size of less than 1 μm in all dimensions, without being limited thereto. The pharmaceutical compositions of the present invention as prepared by any one of these preparation processes are typically obtained in solid or semi-solid form e.g. as a solidified extrudate, a powder or mass of gel- or paste-like consistency and may thus be in particular conveniently used to provide solid or semi-solid dosage forms comprising a pharmaceutical compositions according to the present invention. The solid dosage form can e.g. be a powder, a lozenge, a suppository, a tablet or a filled capsule. Suitable semi-solid dosage forms can be exemplified by gels, creams, pastes and ointments.

For oral administration tablets and capsules have particularly good acceptance among most patients and are thus preferably used as delivery system. Tablets comprising the pharmaceutical composition of the present invention may readily be prepared by conventional pressing of the raw powder or melt extrusion of the pharmaceutical composition and re-solidification using dies of the desired tablet size and shape. In case the as prepared composition is semi-solid one or more fillers, which can be of the above-mentioned type, may be added for thickening in order to achieve the desired consistency for providing tablets. Capsules filled with the pharmaceutical composition according to the present invention may be prepared using processing techniques and equipment, which is per se known from the prior art, e.g. from E. T. Cole, Advanced Drug Delivery Reviews 60 (2008), 747-756. Both capsules of the soft type and of the hard type can be used to encapsulate the inventive pharmaceutical compositions. Soft capsules are typically formed and filled in one operation using a rotary die and have a shell consisting of a single piece. Hard capsules are usually manufactured separately and consist of a cap and a body. The empty body may be filled with the targeted amount of the pharmaceutical composition according to the present invention e.g. in powder form or as hot extruded melt. Subsequently the cap is attached and the capsule sealed e.g. by applying a band of adhesive material at the body/cap interface or by moisturizing the contact area between body and cap, heating and setting. The capsule shell material comprises typically gelatin as main constituent although alternative materials such as hydroxypropyl methylcellulose, iota carrageenan, hydroxypropyl starch, polyvinyl alcohol and starch may also be used. The shell may include additional substances e.g. plasticizers such as water or glycerol, coloring agents and opacifiers.

Owing to the efficient solubilisation of APIs by the polyalkoxylated alcohols of the present invention an effective dose as required for most medical applications in-vivo may usually be provided by a single unit of a tablet or capsule of conventional size and within a short time from administration.

The present invention will be illustrated in more detail by the following Examples, however, the invention is not meant to be limited to these.

EXAMPLES

Unless otherwise mentioned, all parts and percentages are by weight.

Example 1

Synthesis of Polyalkoxylated Alcohols of the Type
R—O—$(BO)_m$-$(EO)_n$—H

Eight sets of polyalkoxylated alcohols having a diblock structure corresponding to the formula R—O—$(BO)_m$-$(EO)_n$—H with three distinct degrees of ethoxylation for each set were prepared using the two stage high throughput method described in the following. Table 1 shows the targeted compositions of the intermediates R—O—$(BO)_m$—H after the first stage (designated as intermediates A to H) and of the final polyalkoxylated alcohols (A-1 to H-3).

TABLE 1

Targeted compositions of the prepared intermediates R—O—$(BO)_m$—H (designated as A to H) and final polyalkoxylated alcohols R—O—$(BO)_m$—$(EO)_n$—H (designated as A-1 to H-3)

| Sample # | Intermediate | Polyalkoxylated alcohol | | |
|---|---|---|---|---|
| | | 1 | 2 | 3 |
| A | $R^1$—O—$(BO)_4$—H | $R^1$—O—$(BO)_4$-$(EO)_{16}$—H | $R^1$—O—$(BO)_4$-$(EO)_{24}$—H | $R^1$—O—$(BO)_4$-$(EO)_{30}$—H |
| B | $R^1$—O—$(BO)_8$—H | $R^1$—O—$(BO)_8$-$(EO)_{16}$—H | $R^1$—O—$(BO)_8$-$(EO)_{24}$—H | $R^1$—O—$(BO)_8$-$(EO)_{30}$—H |

TABLE 1-continued

Targeted compositions of the prepared intermediates R—O—(BO)$_m$—H (designated as A to H) and
final polyalkoxylated alcohols R—O—(BO)$_m$—(EO)$_n$—H (designated as A-1 to H-3)

| Sample # | Intermediate | Polyalkoxylated alcohol 1 | Polyalkoxylated alcohol 2 | Polyalkoxylated alcohol 3 |
|---|---|---|---|---|
| C | R$^2$—O—(BO)$_4$—H | R$^2$—O—(BO)$_4$-(EO)$_{16}$—H | R$^2$—O—(BO)$_4$-(EO)$_{24}$—H | R$^2$—O—(BO)$_4$-(EO)$_{30}$—H |
| D | R$^2$—O—(BO)$_8$—H | R$^2$—O—(BO)$_8$-(EO)$_{16}$—H | R$^2$—O—(BO)$_8$-(EO)$_{24}$—H | R$^2$—O—(BO)$_8$-(EO)$_{30}$—H |
| E | R$^3$—O—(BO)$_4$—H | R$^3$—O—(BO)$_4$-(EO)$_{16}$—H | R$^3$—O—(BO)$_4$-(EO)$_{24}$—H | R$^3$—O—(BO)$_4$-(EO)$_{30}$—H |
| F | R$^4$—O—(BO)$_8$—H | R$^4$—O—(BO)$_8$-(EO)$_{16}$—H | R$^4$—O—(BO)$_8$-(EO)$_{24}$—H | R$^4$—O—(BO)$_8$-(EO)$_{30}$—H |
| G | R$^5$—O—(BO)$_8$—H | R$^5$—O—(BO)$_8$-(EO)$_{16}$—H | R$^5$—O—(BO)$_8$-(EO)$_{24}$—H | R$^5$—O—(BO)$_8$-(EO)$_{30}$—H |
| H | R$^6$—O—(BO)$_8$—H | R$^6$—O—(BO)$_8$-(EO)$_{16}$—H | R$^6$—O—(BO)$_8$-(EO)$_{24}$—H | R$^6$—O—(BO)$_8$-(EO)$_{30}$—H |

R$^1$: n-dodecyl
R$^2$: 2-ethyl-hexyl
R$^3$: farnesyl
R$^4$: neryl
R$^5$: cinnamyl
R$^6$: (1R)-(−)-myrtenyl The alkoxylation reactions were conducted in two stages in a Symyx PPR® (Parallel Pressure Reactor) setup containing 48 small reactor cells (6 modules each having 8 cells) with glass inserts and equipped with removable PEEK paddles for mechanical stirring.

In the first stage the intermediates A-H of the type R—O—(BO)$_m$—H as listed in Table 1 were prepared in triplicate each using three modules, i.e. in total 24 cells of the Symyx PPR® setup, by butoxylation of the corresponding precursor alcohols R—OH. For each cell, a glass insert and a removable PEEK stir paddle were dried in a vacuum oven at 125° C. overnight. Starting solutions were prepared from the precursor alcohols R—OH (A, B: 1-dodecanol, 98+% (A.C.S. reagent); C, D: 2-ethyl-1-hexanol, 99.6%; E: farnesol, 95% (mixture of isomers); F: nerol, 97%; G: cinnamyl alcohol, 98%; H: (1R)-(−)-myrtenol, 95%; all purchased from Sigma-Aldrich) each by dissolving therein potassium in an amount of about 1 wt. % based on the weight of the alcohol. Herein, 1-dodecanol and cinnamyl alcohol were heated to a temperature slightly above their respective melting point (22-26° C. or 33-35° C., respectively) to keep them in a liquid state. An aliquot of the respective starter solution corresponding to a targeted amount of 6-10 mmol of the alcohol was each charged manually using a pipette into the glass insert for the respective reaction cell under nitrogen and the mass of the starting material in each insert was recorded. The glass inserts were loaded into the corresponding PPR wells and the stirring paddles attached. Subsequently, the reactor cells were sealed, heated to 110° C. and pressurized with nitrogen to a pressure of 345 kPa (50 psi). Then the corresponding 24 reactor cells were each charged by using a Cavro robotic arm connected to the Symyx PPR® setup with the calculated amount of 1,2-butylene oxide (99+%, purchased from Sigma-Aldrich) corresponding to the targeted length of the (BO)$_m$ block assuming complete consumption of the butylene oxide in the butoxylation reaction of the precursor alcohols. Subsequently, the temperature was increased to 150° C. and the reaction mixtures were stirred for 3 hours at this temperature. The reactor was then cooled and the cells were vented and purged with nitrogen to remove residual butylene oxide. The glass inserts were then removed from the reactors, and the resulting material obtained from the triplicate runs for each targeted type of intermediate as listed in Table 1 was combined. Thus eight samples corresponding to intermediates A-H were obtained. A portion of each of these samples was set aside for molecular weight analysis of the intermediates as set forth below.

The remaining amounts of the prepared intermediates were used as starting material for ethoxylation in the second stage of the preparation process to synthesize the 24 targeted polyalkoxylated alcohols A1 to H3 as listed in Table 1. Each of the polyalkoxylated alcohols of Table 1 was synthesized in duplicate, i.e. a set of samples corresponding to targeted compounds A1 to H3 was prepared in modules 1-3 and a second set of samples (not shown) having the same targeted compositions was prepared in modules 4-6 of the Symyx PPR® setup. Accordingly the remaining amount of each of the eight R—O—(BO)$_m$—H intermediates prepared in the first stage was divided in six parts of comparable mass that were placed into six glass inserts to give a total of 48 filled glass inserts. The mass of material in each insert was recorded. The inserts were then loaded into the designated PPR wells, and the stirring paddles were attached. Subsequently, the reactor cells were sealed, heated to 60° C., and pressurized with nitrogen to a pressure of 345 kPa (50 psi). Ethylene oxide (99.99%) purchased from ARC Specialty Products was then delivered to each of the 48 cells via an Isco syringe pump equipped with a robotically controlled needle and compressed gas microvalve connected to the Symyx PPR® setup. The amount of added ethylene oxide was each calculated to correspond to the desired length of the (EO)$_n$ block of the respective targeted final polyalkoxylated alcohol as listed in Table 1 assuming almost complete consumption of the ethylene oxide in the ethoxylation reaction of the intermediates. After the addition of ethylene oxide, the temperature was increased to 150° C. and the reaction mixtures were stirred for 3 hours at this temperature. After cooling and venting as described above for the first stage, the mass of each glass inset with the resulting product was measured to determine the effectively added amount of ethylene oxide each. The obtained mixtures were quenched with 1 M aqueous solution of acetic acid (Fisher Scientific) using the PPR robots, resealing the reactors and stirring for one hour. The quenched mixtures were then dried under reduced pressure using a vacuum pump.

The resulting samples of polyalkoxylated alcohols R—O—(BO)$_m$-(EO)$_n$—H were used without further purification for molecular weight analysis and the preparation of pharmaceutical compositions as set forth below.

Molecular Weight Determination

The molecular weight distributions of the prepared intermediates R—O—(BO)$_m$—H were determined by liquid chromatography/electrospray ionization-mass spectrometry (LC/ESI-MS) in the positive ion (PI) mode. For this purpose the as-prepared intermediates were each dissolved in methanol in an amount of 3 mg/mL. 2 μL aliquots of these solutions were injected to a Waters Alliance 2795 ternary gradient liquid chromatograph coupled to a Micromass LCT_premier, SN #KD-184, time of flight MS system via a Micromass Z-spray electrospray (ESI) interface operating in the PI mode.

The following analysis conditions were used:
Column: None Flow Injection
Mobile phase: 0.03 M ammonium acetate in methanol
Flow rate: 1.0 mL/min (split 2:1)
ESI conditions: Source Block: 110° C.; Desolvation: 250° C.; Capillary: 2.5 kV; Cone: 100V
MS conditions: MCP: 2,300V; Mode: +TOFMS; Continuum; Resolution 10,000 (+)
Scan: 50 to 2,800 amu (+); Rate: 1.0 sec/scan
Lock Spray: –10 μL/min of (556.2713 amu (+))—(YGGFL)

As the detected ions were adducts of the respective intermediate with an ammonium ion, the experimental molecular weight data were corrected by subtracting the molecular weight of the ammonium ion, M(NH$_4^+$): 18 amu, to yield values representative for the intermediate itself. Table 2 shows the number average molecular weight (M$_n$), the weight average molecular weight (M$_w$) and the polydispersity index (M$_w$/M$_n$) calculated accordingly from the obtained experimental molecular weight distributions for the prepared intermediates. Table 2 further comprises the average number of BO units per molecule, m, for each prepared intermediate, which were calculated by subtracting the molecular weight of the respective precursor alcohol, M(R—OH), from M$_n$ of the intermediate.

TABLE 2

M$_n$, M$_w$, and M$_w$/M$_n$ and calculated average number of BO units per molecule (m) for the prepared intermediates R—O—(BO)$_m$—H as derived by LC/ESI-MS analysis

| Intermediate | R | M$_n$ [g/mol] | M$_w$ [g/mol] | M$_w$/M$_n$ | m |
|---|---|---|---|---|---|
| A | R$^1$ | 553 | 568 | 1.03 | 5.1 |
| B | R$^1$ | 702 | 739 | 1.05 | 7.2 |
| C | R$^2$ | 539 | 557 | 1.03 | 5.7 |
| D | R$^2$ | 683 | 710 | 1.04 | 7.7 |
| E | R$^3$ | 551 | 574 | 1.04 | 4.6 |
| F | R$^4$ | 658 | 683 | 1.04 | 7.0 |
| G | R$^5$ | 642 | 677 | 1.05 | 7.1 |
| H | R$^6$ | 701 | 725 | 1.03 | 7.6 |

R$^1$-R$^6$: as defined for Table 1

The molecular weight distributions of the polyalkoxylated alcohols R—O—(BO)$_m$-(EO)$_n$—H prepared from the intermediates as set forth above were studied by size exclusion chromatography (SEC) using a Polymer Labs 3 μm Mixed-E and a Polymer Labs 3 μm 100 Å column held at a temperature of 35° C., connected to a Waters Model 2690 injector and pump and a Waters 410 DRI detector with a sensitivity of 128 and a scale factor of 1, operated at a temperature of 35° C. Approximately 0.02 g of the polyalkoxylated alcohol to be investigated were dissolved in 10 mL of tetrahydrofuran. 50 μL of this solution were injected through the injector into the chromatographic system for the analysis. Tetrahydrofuran (Fisher Scientific HPLC grade) was used as eluent. The pump was set to a nominal flow rate of 1.0 mL/min Data acquisition was achieved by the Polymer Laboratories Calibre GPC/SEC acquisition version 6.0 and reanalysis version 7.04 software. Polystyrene standards with a narrow molecular weight distribution available from Agilent Technologies (part no. PL 2012-2001, -3001, -6001, -7001 and -9001 and PL 2013-1001, -2001 and -3001) were used for calibration.

From the measured molecular weight distributions M$_n$, M$_w$ and M$_w$/M$_n$ were calculated and are listed in Table 3 for the prepared polyalkoxylated alcohols A-1 to H-3. Table 3 moreover includes the average number of BO units per molecule (m) determined as set forth above for the intermediate used to prepared the respective polyalkoxylated alcohol (cf. Table 2), the average number of EO units per molecule (n), the average total degree of alkoxylation (n+m) and the ratio n/m. The average number of EO units per molecule was calculated for each prepared polyalkoxylated alcohol using the following formula:

$$n = \{M_n[R\text{—O—}(BO)_m\text{-}(EO)_n\text{—H}] - M_n[R\text{—O—}(BO)_m\text{—H}]\}/M(EO)$$

wherein M$_n$[R—O—(BO)$_m$-(EO)$_n$—H] represents the number average molecular weight determined by the SEC analysis for the respective polyalkoxylated alcohol, M$_n$[R—O—(BO)$_m$—H] is the number average molecular weight determined for the corresponding intermediate by LC/ESI-MS analysis as set forth above and M(EO) is the molecular weight of a single EO unit. The data in Table 3 indicates a relatively high deviation of the actual composition from the respective targeted composition for at least some of the prepared polyalkoxylated alcohols. This may at least partly be due to an incomplete consumption of alkylene oxide in the alkoxylation reaction and the preparation of the polyalkoxylated alcohols being conducted on a small scale, which generally causes higher deviations of the product composition from the targeted stoichiometry compared to the corresponding preparation on a commercial scale. However, the objective was not to precisely reach the targeted stoichiometries as listed in Table 1, but to synthesize a broad range of polyalkoxylated alcohols in an efficient manner for testing their capabilities as excipients for drugs. Deviations from the targeted stoichiometry are not critical to the present invention as long as the actual stoichiometry of the polyalkoxylated alcohol used as excipient fulfills the criteria as set forth in the claims. If a close match of targeted and actual composition is desired the polyalkoxylated alcohols according to the present invention could be prepared by applying the procedure as set forth above on a larger scale.

TABLE 3

M$_n$, M$_w$, M$_w$/M$_n$, m, n, (n + m) and n/m of the prepared polyalkoxylated alcohols R—O—(BO)$_m$—(EO)$_n$—H

| Polyalkoxylated alcohol | R | M$_n$ [g/mol] | M$_w$ [g/mol] | M$_w$/M$_n$ | n | m | n + m | n/m |
|---|---|---|---|---|---|---|---|---|
| A-1 | R$^1$ | 1,500 | 1,930 | 1.29 | 21.5 | 5.1 | 26.6 | 4.2 |
| A-2 | R$^1$ | 1,830 | 2,360 | 1.29 | 29.0 | 5.1 | 34.1 | 5.7 |
| A-3 | R$^1$ | 1,880 | 2,430 | 1.29 | 30.2 | 5.1 | 35.3 | 5.9 |
| B-1 | R$^1$ | 1,730 | 2,160 | 1.25 | 23.4 | 7.2 | 30.6 | 3.2 |
| B-2 | R$^1$ | 2,020 | 2,630 | 1.30 | 30.0 | 7.2 | 37.2 | 4.2 |
| B-3 | R$^1$ | 2,190 | 2,840 | 1.30 | 33.8 | 7.2 | 41.0 | 4.7 |
| C-1 | R$^2$ | 1,220 | 1,640 | 1.34 | 15.5 | 5.7 | 21.2 | 2.7 |

TABLE 3-continued $M_n$, $M_w$, $M_w/M_n$, m, n, (n + m) and n/m of the prepared polyalkoxylated alcohols R—O—(BO)$_m$—(EO)$_n$—H

| Poly-alkoxylated alcohol | R | $M_n$ [g/mol] | $M_w$ [g/mol] | $M_w/M_n$ | n | m | n + m | n/m |
|---|---|---|---|---|---|---|---|---|
| C-2 | $R^2$ | 1,520 | 2,020 | 1.33 | 22.3 | 5.7 | 28.0 | 3.9 |
| C-3 | $R^2$ | 1,610 | 2,130 | 1.32 | 24.3 | 5.7 | 30.0 | 4.3 |
| D-1 | $R^2$ | 1,580 | 2,060 | 1.30 | 20.4 | 7.7 | 28.1 | 2.6 |
| D-2 | $R^2$ | 1,830 | 2,430 | 1.33 | 26.1 | 7.7 | 33.8 | 3.4 |
| D-3 | $R^2$ | 1,880 | 2,470 | 1.31 | 27.2 | 7.7 | 34.9 | 3.5 |
| E-1 | $R^3$ | 1,170 | 1,600 | 1.37 | 14.1 | 4.6 | 18.7 | 3.1 |
| E-2 | $R^3$ | 1,160 | 1,610 | 1.39 | 13.8 | 4.6 | 18.4 | 3.0 |
| E-3 | $R^3$ | 1,460 | 2,110 | 1.45 | 20.7 | 4.6 | 25.3 | 4.5 |
| F-1 | $R^4$ | 1,410 | 1,900 | 1.35 | 17.1 | 7.0 | 24.1 | 2.4 |
| F-2 | $R^4$ | 1,620 | 2,240 | 1.38 | 21.9 | 7.0 | 28.9 | 3.1 |
| F-3 | $R^4$ | 1,750 | 2,450 | 1.40 | 24.8 | 7.0 | 31.8 | 3.5 |
| G-1 | $R^5$ | 1,200 | 1,680 | 1.40 | 12.7 | 7.1 | 19.8 | 1.8 |
| G-2 | $R^5$ | 1,410 | 2,000 | 1.42 | 17.5 | 7.1 | 24.6 | 2.5 |
| G-3 | $R^5$ | 1,420 | 2,020 | 1.42 | 17.7 | 7.1 | 24.8 | 2.5 |
| H-1 | $R^6$ | 1,400 | 1,840 | 1.31 | 15.9 | 7.6 | 23.5 | 2.1 |
| H-2 | $R^6$ | 1,610 | 2,170 | 1.35 | 20.7 | 7.6 | 28.3 | 2.7 |
| H-3 | $R^6$ | 1,550 | 2,120 | 1.37 | 19.3 | 7.6 | 26.9 | 2.5 |

$R^1$-$R^6$: as defined for Table 1

Example 2 a) Synthesis of Solid Drug/Excipient Mixtures

The synthesized polyalkoxylated alcohols according to Table 3 were evaluated as excipients in mixtures with four different model drugs, namely Ketoprofen and Danazol purchased from Spectrum Chemical MFG Group, and Griseofulvin and Probucol purchased from Sigma-Aldrich. Concentrated Ketoprofen/excipient mixtures were prepared using the following high-throughput method. A polystyrene plate with 96 wells in a 12×8 array was used as a plate for the preparation of concentrated initial suspensions. The plate was placed on a Tecan 150 chill platform, and an 128 µL aliquot of a 1.0 wt. % aqueous solution of the respective polyalkoxylated alcohol was robotically delivered into the respective designated well. After such delivery of aqueous solutions of the polyalkoxylated alcohols to all wells the plate was cooled to 4° C. by the Tecan 150 chill platform. Then the chill platform with this plate was shaken and a 32 µL aliquot of a 4.0 wt. % solution of Ketoprofen in methanol was quickly injected into each excipient solution. The drug immediately co-precipitated with the excipients forming small microparticles. The plate with the concentrated drug/excipient suspensions was continuously shaken to prevent settling of a solid component, and 25 µL aliquots of these suspensions were transferred into the wells of a second polystyrene plate with 96 wells each filled previously with 175 µL of deionized water to yield 200 µL of suspensions with intermediate concentration each. The second plate with drug/excipient suspensions of intermediate concentration was also shaken to prevent settling of a solid component, and 25 µL aliquots of these suspensions were again transferred into the wells of a third polystyrene plate with 96 wells each filled previously with 175 µL of water to yield 200 µL of dilute suspensions each. The plate with the dilute suspensions was prepared in triplicate. Those plates with dilute suspensions were then placed into a bench-top freeze dryer (VirTis model Advantage EL), where the samples were cooled to −40° C., and then freeze-dried overnight at that temperature. This procedure resulted in the formation of solid drug/excipient mixtures. Drug/excipient mixtures with Danazol, Griseofulvin and Probucol, respectively, instead of Ketoprofen as drug component were prepared using the same high throughput method described above for the preparation of Ketoprofen/excipient mixtures except that the following solutions were employed in the preparation of the concentrated initial suspensions: 0.5 wt. % aqueous solution of the respective polyalkoxylated alcohol and a 1.0 wt. % solution of Danazol or Probucol in methanol or a 1.0 wt. % solution of Griseofulvin in N,N-dimethylformamide (DMF). For turbidity analysis moreover a set of reference samples were prepared following the foregoing method, but without addition of any drug, yielding freeze-dried excipients.

b) Characterization of Solid Drug/Excipient Mixtures

The extent and rate of dissolution of drugs from the prepared solid drug/excipient mixtures in water were studied by turbidimetry and optical microscopy.

For turbidity analysis a multi-well plate with the freeze-dried drug/excipient mixtures to be measured in the individual wells prepared as set forth above was placed into the chamber of a Nepheloskan Ascent instrument from ThermoLabsystem and 190 µL of deionized water were robotically added into the first well. The platform with the plate was shaken for 5 s and turbidity measurements were taken each 3 s over 300 s. After this, deionized water (190 µL) was robotically added into a second well, the platform was shaken again, and turbidity was measured in the described manner over 300 s for this second sample. This procedure was repeated until all freeze-dried samples in the plate were analyzed. Table 4 reports the turbidity in relative nephelometry units (RNU) for selected drug/excipient mixtures measured 30 s and 300 s after the addition of water, respectively.

TABLE 4

Turbidity measured for selected mixtures of drugs with different polyalkoxylated alcohols according to the invention listed in Table 3 as excipients 30 s and 300 s after the addition of water

| Example | Excipient | Drug | Concentration (Excipient) [mg/L] | Concentration (Drug) [mg/L] | Turbidity (after 30 s) [RNU] | Turbidity (after 300 s) [RNU] |
|---|---|---|---|---|---|---|
| T-1 | A-3 | Ketoprofen | 131.6 | 103.9 | 2.30 | 1.89 |
| T-2 | D-3 | Ketoprofen | 131.6 | 103.9 | 3..57 | 1.71 |

TABLE 4-continued

Turbidity measured for selected mixtures of drugs with different polyalkoxylated alcohols according to the invention listed in Table 3 as excipients 30 s and 300 s after the addition of water

| Example | Excipient | Drug | Concentration (Excipient) [mg/L] | Concentration (Drug) [mg/L] | Turbidity (after 30 s) [RNU] | Turbidity (after 300 s) [RNU] |
|---|---|---|---|---|---|---|
| T-3 | H-3 | Danazol | 65.8 | 26.0 | 6.36 | 5.85 |
| T-4 | F-3 | Griseofulvin | 65.8 | 26.0 | 2.33 | 4.85 |
| T-5 | G-3 | Griseofulvin | 65.8 | 26.0 | 0.76 | 0.78 |
| T-6 | C-3 | Probucol | 65.8 | 26.0 | 3.08 | 8.74 |
| T-7 | C-2 | Probucol | 65.8 | 26.0 | 1.62 | 1.34 |
| T-8 | C-1 | Probucol | 65.8 | 26.0 | 1.18 | 1.42 |
| T-9 | D-3 | Probucol | 65.8 | 26.0 | 2.49 | 2.41 |
| T-10 | D-2 | Probucol | 65.8 | 26.0 | 7.73 | 10.19 |
| T-11 | D-1 | Probucol | 65.8 | 26.0 | 3.92 | 4.04 |
| T-12 | E-3 | Probucol | 65.8 | 26.0 | 0.96 | 0.90 |
| T-13 | E-2 | Probucol | 65.8 | 26.0 | 2.85 | 2.70 |
| T-14 | E-1 | Probucol | 65.8 | 26.0 | 1.28 | 1.46 |
| T-15 | F-3 | Probucol | 65.8 | 26.0 | 1.99 | 1.99 |
| T-16 | F-2 | Probucol | 65.8 | 26.0 | 4.71 | 4.74 |
| T-17 | F-1 | Probucol | 65.8 | 26.0 | 1.16 | 1.52 |
| T-18 | G-3 | Probucol | 65.8 | 26.0 | 8.15 | 7.66 |
| T-19 | G-2 | Probucol | 65.8 | 26.0 | 1.27 | 1.22 |
| T-20 | G-1 | Probucol | 65.8 | 26.0 | 1.50 | 2.14 |
| T-21 | H-3 | Probucol | 65.8 | 26.0 | 20.10 | 20.25 |
| T-22 | H-2 | Probucol | 65.8 | 26.0 | 0.92 | 1.09 |
| T-23 | H-1 | Probucol | 65.8 | 26.0 | 3.13 | 5.63 |

The reference samples of freeze-dried excipient solutions were analyzed by turbidimetry according to the same procedure. These solutions of the polyalkoxylated alcohols according to the invention consistently showed a turbidity below 1.5 RNU. Therefore higher turbidity values observed for the drug/excipient mixtures originate from undissolved drug and not from the excipient.

Moreover, wet-milled drug suspensions were analyzed as reference samples to determine the turbidity of the drugs in the absence of excipients. The suspensions were prepared by wet milling of Griseofulvin, Danazol and Probucol, respectively, using yttrium-stabilized zirconia milling beads. 78.6 g of yttrium-stabilized zirconia grinding beads (YTZ from Tosoh Corp., diameter: 0.5 mm) were provided in a 50 mL plastic bottle and 10.0 g deionized water and 0.54 g of the respective drug were added. In the case of Probucol, a dispersant, Daxad 19LS (from Hampshire Chem. Corp.), was added in an amount corresponding to 1 wt. % of the mass of Probucol to counteract coating of the milling beads by the drug. The resulting mixture was placed on a rotating ball mill for 24 h. Subsequently 11.06 g of deionized water were added, the suspension was shaken extensively and then separated from the milling beads. An aliquot of 0.20 g of this suspension was further diluted with 49.80 g of deionized water to yield a suspension having a nominal drug concentration of 0.01 wt. %, which was then analyzed for its turbidity using a Nepheloskan Ascent instrument from ThermoLabsystem. Wet milling of Ketoprofen was omitted due to its comparatively high solubility in water. Table 5 summarizes the measured turbidity of the wet milled reference drug suspensions along with the average particle size of the suspended drug particles measured using a 90 Plus Particle Size Analyzer instrument from Brookhaven Instruments Corp. and literature values for the aqueous solubility of the drugs.

TABLE 5

Average particle size and turbidity of wet milled reference drug suspensions, and literature values for the aqueous solubility of the drugs

| Reference Example | Drug | Particle size [μm] | Turbidity[a] [RNU] | Aq. Solubility [mg/L] |
|---|---|---|---|---|
| T-24 | Griseofulvin | 3.8 | 137 | 8.64[b] |
| T-25 | Danazol | 3.6 | 69 | 0.50[c] |
| T-26 | Probucol | 0.4 | 94 | 0.042[b] |

[a]average value of three turbidity measurements
[b]taken from http://www.drugbank.ca
[c]Eur. J. Biopharm. 68 (2008), 330-337.

The drug/excipient mixtures listed in Table 4 show much lower turbidity (with the only exception of Example T-21, which is probably due to an artifact) than the reference samples T-24 to T-26, which may only in part be attributed to the lower drug concentration of 26.0 mg/L (T-3 to T-23) versus 100 mg/L in case of the suspensions of the pure drugs (T-24 to T-26). This suggests that substantial portions of the drug contained in the initial solid drug/excipient mixtures dissolved in the aqueous medium, meaning a major enhancement of the drug solubility by the excipient. For instance, Probucol will be present in the reference sample T-26 having a nominal drug concentration of 100 mg/L almost completely in undissolved suspended form due to the very low solubility of neat Probucol in water of merely 0.042 mg/L. Assuming a linear relationship between the concentration of undissolved drug and the turbidity, a turbidity value of ~24 RNU is calculated for a suspension containing Probucol in an amount of 26 mg/L, which corresponds to the nominal drug concentration in Examples T-6 to T-23. However, all of these Examples showed significantly lower turbidity, in cases of Examples T-7, T-8, T-12, T-14, T-15, T-17, T-19 and T-22 even below 2 RNU suggesting that more than 90 wt. % of the Probucol in these samples was dissolved, i.e. the Probucol concentration in solution being more than 20 mg/L. This illustrates that the polyalkoxylated alcohols according to the invention enable a dramatic increase of the solubility of poorly water soluble drugs. Furthermore, the comparatively small difference between the turbidity values measured for an individual sample on the one hand 30 s after the addition of water and secondly 300 s after the addition of water, shows that the dissolution of the drug occurred fast and was accomplished at least to a large extent within 30 s.

These findings were also confirmed by observing the behaviour of the drug/excipient mixtures upon addition of water using optical microscopy. For this purpose images were taken of the respective freeze-dried sample prepared as set forth above in the dry state as well as immediately after and 300 s after the addition of 190 µL of deionized water to the sample at 10 fold magnification using an Olympus 1X81 optical microscope. Particular care was taken to depict a domain in the viewing area that is visually representative for the whole sample. The drugs were found to dissolve from the solid mixtures with the polyalkoxylated alcohols according to the invention in water to a large extent leaving hardly any visible solid residues after 300 s from the addition of water. This is illustrated for a mixture of Probucol and the polyalkoxylated alcohol C-2 corresponding to Example T-7 of Table 4 in FIG. 1.

Example 3 a) Synthesis of Semi-Solid Drug/Excipient Mixtures

Semi-solid mixtures of Probucol as a poorly water soluble model drug with different excipients as listed in Table 6, namely selected synthesized polyalkoxylated alcohols according to the invention and some commercially available excipients for comparison, were prepared. In each case a first solution was prepared by dissolving 0.20 g of Probucol in 4.80 g methanol (Fisher Scientific; HPLC grade), and a second solution was prepared by dissolving 0.60 g of the respective excipient in 14.40 g methanol. These two solutions were then mixed to provide 20.00 g of a clear solution with a probucol/excipient weight ratio of 1:3. Subsequently methanol was removed using a rotary evaporator for 30 min at ambient temperature followed by drying with a Cenco Hyvac 7 high vacuum pump for 30 min at ambient temperature and a pressure of 1.33 Pa yielding a visually homogeneous semi-solid drug/excipient residue each.

b) Preparation of Capsules

Vcaps® size "0" capsules (produced by Capsugel) each filled with one of the prepared semi-solid probucol/excipient mixtures were prepared. The mass of an empty capsule was measured. About 100 mg of the respective Probucol/excipient mixture were manually loaded into a capsule. The mass of the filled capsule was taken, in order to determine the exact mass of the Probucol/excipient mixture in the capsule. The capsule was subsequently sealed by applying a thin film of 20 wt % aqueous hydroxypropyl methyl cellulose (HPMC; Methocel Premium LV F5, manufactured by Dow Chemical) on the rim of the capsule body, and placing the capsule cap on the capsule body so that the overlapping part is sealed with HPMC.

c) Measurement of Probucol Solubility

The effect of the different excipients in the semi-solid drug/excipient mixtures as listed in Table 6 on the solubility of Probucol in aqueous medium was analyzed as follows. A capsule filled with the respective mixture, prepared as set forth above and stored at ambient conditions (22° C., 50% RH) for 7 days, was placed in a beaker that contained phosphate buffer of pH 6.5 in an amount calculated to correspond to 1 mL per mg of Probucol in the capsule. The phosphate buffer of pH 6.5 was prepared by dissolving 4.80 g sodium chloride (Sigma-Aldrich; 99+%, A.C.S. reagent), 5.36 g sodium hydrogenphosphate heptahydrate (Sigma-Aldrich; 98+%, A.C.S. reagent) and 6.36 g potassium dihydrogenphosphate (Sigma-Aldrich; 99+%, A.C.S. reagent) in 500 mL of pure filtered water, followed by adjustment of the resulting solution to pH 6.50 using 30 wt % solution of sodium hydroxide (Sigma-Aldrich; 97+%) in pure filtered water. The buffer solution with the capsule was magnetically stirred at ambient temperature until the capsule broke. From this point in time the stirring was continued for additional 30 min. Subsequently an aliquot of the resulting dispersion having a volume of about 2 mL was filtered using a disposable syringe filter (Whatman; nylon, 0.2 µm pore size with GMF 150 prefilter). A 30.0 µL aliquot of this filtrate was transferred into a vial with 150.0 µL methanol (Fisher Scientific; HPLC grade), the vial was sealed, and gently agitated for a several seconds to mix. The Probucol concentration in the resulting sample was determined by high pressure liquid chromatography (HPLC) analysis using an Agilent 1100 HPLC system with Agilent Zorbax XDB C8 analytical column (4.6 mm×150 mm) and Agilent 1100 diode array detector (detection wavelength: 254 nm) at a temperature of 30° C. The injection volume of the sample was 2.0 µL. As eluent a mixture of water and acetonitrile (65:35) was employed at a flow rate of 1.00 mL/min. For calibration four Probucol solutions in methanol having Probucol concentrations of 25.1 mg/L, 50.0 mg/L, 75.2 mg/L and 106.6 mg/L were used. The area of the Probucol peak at a retention time of about 7.51 min was measured and exhibited linear correlation ($R^2$=0.9957) with the Probucol concentration. The solubilities of Probucol determined by the HPLC analysis for the different investigated semi-solid probucol/excipient mixtures are summarized in Table 6 as well as the corresponding calculated increase in Probucol solubility relative to the reported solubility of neat Probucol in water of 0.042 mg/L. The values reported in Table 6 are average values from 2 or 3 individual measurements each.

This procedure was also applied to capsules filled with semi-solid drug/excipient mixture, which were stored at ambient conditions (22° C., 50% RH) for 4 months or at 40° C. and 75% RH for 4 months to investigate the stability of the dissolution characteristics of semi-solid mixtures of Probucol with selected polyalkoxylated alcohols of the type R—O—(BO)$_m$-(EO)$_n$—H according to the present invention. Table 6 includes only the results obtained for the investigated filled capsules that were stored at ambient conditions for 4 months. Correspondingly filled capsules that were subjected to accelerated ageing at 40° C. and 75% RH showed the same increase in Probucol solubility within the limits of experimental error as after 4 months storage at ambient conditions.

TABLE 6

Probucol solubility in phosphate buffer pH 6.5 at 22° C. for semi-solid mixtures of Probucol with different excipients, filled in capsules and stored for 7 days or 4 months, respectively, at ambient conditions, and calculated solubility increase relative to the solubility of neat Probucol in water

| Sample | Excipient | After 7 days at ambient conditions | | After 4 months at ambient conditions | |
|---|---|---|---|---|---|
| | | Probucol solubility [mg/L] | Solubility increase[1] | Probucol solubility [mg/L] | Solubility increase[1] |
| K-1 | E-3 | 269 | 6,400 x | 278 | 6,620 x |
| K-2 | F-3 | 246 | 5,860 x | N/m | N/m |
| K-3 | G-2 | 232 | 5,520 x | 219 | 5,210 x |
| K-4 | H-2 | 329 | 7,830 x | 330 | 7,860 x |
| K-5 (Comp. Ex.) | Pluronic F-127[a] | 52.9 | 1,260 x | N/m | N/m |
| K-6 (Comp. Ex.) | mPEG 1000[b] | 6.1 | 145 x | N/m | N/m |
| K-7 (Comp. Ex.) | HPMC-AS MF[c] | 11.8 | 280 x | N/m | N/m |
| K-8 (Comp. Ex.) | PVP 29K[d] | 117 | 2790 x | N/m | N/m |
| K-9 (Comp. Ex.) | Eumulgin RO35 PH[e] | 186 | 4430 x | N/m | N/m |

[a] non-ionic EO-PO-EO block copolymer available from BASF
[b] poly(ethylene glycol) methyl ether, $M_n$~1,000 g/mol produced by Dow Chemical
[c] hypromellose acetate succinate grade MF available from Shin-Etsu Chemical
[d] polyvinyl pyrrolidone, $M_n$~29,000 g/mol available from BASF
[e] castor oil alkoxylated with ~35 EO units available from Cognis
[1] calculated relative to the reported solubility of neat probucol in water of 0.042 mg/L
N/m: not measured The results in Table 6 show that the polyalkoxylated alcohols according to this invention can be used very efficiently as excipients to enhance the solubility of a lipophilic drug such as Probucol in aqueous medium. The enhancement of Probucol solubility is significantly higher for semi-solid mixtures of Probucol with these compounds than for mixtures of the drug with conventional excipients such as block copolymers of ethylene oxide and a higher alkylene oxide, and polyethoxylated monoalcohols or oils as illustrated by the Comparative Examples K-5 to K-9. Compared with Eumulgin RO35 PH, which represents the compound with the best solubilizing capability for most lipophilic active ingredients according to US 2011/0281810 A1 and which is the most efficient solubilizer for Probucol among the investigated conventional excipients, the polyalkoxylated alcohol of Example E-3 yielded for instance about 45% higher increase in Probucol solubility, while with the polyalkoxylated alcohol of Example H-2 the enhancement of Probucol solubility is even almost by a factor of two. Moreover the results in Table 6 show that the substantial increase in the solubility of Probucol in aqueous medium imparted by polyalkoxylated alcohols of the type R—O—(BO)$_m$-(EO)$_n$—H according to the present invention is retained also after storage over a considerable period of time, even if exposed to accelerated ageing conditions. This evidences that pharmaceutical compositions according to the present invention exhibit adequate long term stability of their favorable dissolution characteristics for commercial pharmaceutical applications.

The invention claimed is:

1. Solid or semi-solid pharmaceutical composition comprising
   a) at least one active pharmaceutical ingredient, and
   b) at least one polyalkoxylated alcohol,
   wherein said at least one active pharmaceutical ingredient alone has a solubility in distilled water of pH 7.0 of 10 mg/L or less at a temperature of 22° C. and an atmospheric pressure of 1 atm, and
   wherein said at least one polyalkoxylated alcohol is a polyalkoxylated alcohol of the formula

R—O-(AO)—H wherein R is an unsubstituted alkyl, alkenyl, alkynyl, aryl or aralkyl group, the group R having 7 to 25 carbon atoms, (AO) is a polyoxyalkylene moiety of the composition (BO)$_m$(EO)$_n$ with blockwise arrangement of the constituting oxyalkylene units, wherein m and n represent the average number of oxybutylene (BO) units and oxyethylene (EO) units, respectively, m being a number greater than or equal to 1 and n being a number greater than or equal to 1 under the proviso that (m+n) is less than or equal to 200 and the ratio n/(m) is in the range of 1 to 20.

2. The composition according to claim 1, wherein the at least one active pharmaceutical ingredient alone has a solubility in distilled water of pH 7.0 of 1 mg/L or less at a temperature of 22° C. and an atmospheric pressure of 1 atm.

3. The composition according to claim 1 wherein R has 8 to 20 carbon atoms.

4. The composition according to claim 1, wherein the polyalkoxylated alcohol is derived by alkoxylation of a fatty alcohol or a terpene alcohol.

5. The composition according to claim 1, wherein
   m is at least 2, and/or
   n is at least 8, and/or
   (m+n) is less than or equal to 100, and/or
   n/(m) is in the range from 1.5.

6. The composition of claim 1, wherein the polyalkoxylated alcohol is a polyalkoxylated alcohol with a diblock structure according to the formula R—O—(BO)$_m$-(EO)$_n$—H.

7. The composition according to claim 6, wherein m is at least 4, n is at least 12 and (m+n) is less than or equal to 100, under the proviso that n/m is in the range of 1.5 to 10.

8. The composition of claim 1 comprising further at least one additive selected from the group of fillers, pH regulators, solvents, surfactants, antioxidants, preservative agents, plasticizers, coloring agents, flavouring agents, mineral adjuvants, emollients, lubricants, perfumes and excipients other than the at least one polyalkoxylated alcohol and mixtures of any of the foregoing.

9. The composition of claim 1, wherein the at least one active pharmaceutical ingredient and the at least one polyalkoxylated alcohol are comprised in a weight ratio in the range from 10:1 to 1:100 and/or wherein they are comprised together in an amount corresponding to 1 to 100 wt. %, based on the total weight of the composition.

10. The composition of claim 1 comprising copper ions at a concentration of 0 to below 0.01 wt. %, based on the total weight of the pharmaceutical composition.

11. A solid or semi-solid dosage form comprising the composition according to claim 1.

12. A method of increasing the solubility and/or the dissolution rate of an active pharmaceutical ingredient in an aqueous medium and/or of increasing the bioavailability of an active pharmaceutical ingredient comprising the step of blending the active pharmaceutical ingredient as defined in claim 1 with a polyalkoxylated alcohol as defined in claim 1.

13. The solid or semi-solid dosage form of claim 11 in the form of a tablet comprising the composition or a capsule filled with the composition.

* * * * *